United States Patent
Dykes

(10) Patent No.: US 6,256,454 B1
(45) Date of Patent: Jul. 3, 2001

(54) HUMIDIFIER FOR INFANT WARMING APPARATUS

(75) Inventor: Christopher A. Dykes, Columbia, MD (US)

(73) Assignee: Datex- Ohmeda, Inc., Tewksbury, MA (US)

(*) Notice: Subject to any disclaimer, the term of this patent is extended or adjusted under 35 U.S.C. 154(b) by 0 days.

(21) Appl. No.: 09/548,234

(22) Filed: Apr. 12, 2000

Related U.S. Application Data

(60) Provisional application No. 60/170,275, filed on Dec. 11, 1999, and provisional application No. 60/182,135, filed on Feb. 12, 2000.

(51) Int. Cl.[7] .......................... A61H 33/12; D06F 75/00; F17C 7/04
(52) U.S. Cl. .............................................. 392/403; 600/22
(58) Field of Search .............................. 600/22; 392/403; 261/130

(56) References Cited

U.S. PATENT DOCUMENTS

| | | |
|---|---|---|
| 1,430,548 | 10/1922 | Hogue . |
| 1,749,969 | 3/1930 | Brodin . |
| 2,454,657 | 11/1948 | Kuzmin et al. . |
| 2,847,546 | 8/1958 | Crowley et al. . |
| 3,090,857 | 5/1963 | Oberg . |
| 3,219,795 | 11/1965 | Wiseman . |
| 3,282,266 | 11/1966 | Walker, Jr. . |
| 3,821,947 | * 7/1974 | Schossow ............................ 600/22 |
| 3,987,133 | * 10/1976 | Andra ................................. 261/130 |
| 3,990,441 | 11/1976 | Hoyt et al. . |
| 4,500,480 | 2/1985 | Cambio, Jr. . |
| 4,796,605 | * 1/1989 | Sasaki et al. ......................... 600/22 |
| 4,846,783 | * 7/1989 | Koch et al. .......................... 600/22 |
| 5,242,375 | 9/1993 | McDonouch . |
| 5,330,415 | * 7/1994 | Storti et al. ........................... 600/22 |
| 5,336,156 | 8/1994 | Miller et al. . |
| 5,539,854 | * 7/1996 | Jones et al. ......................... 392/403 |
| 5,616,115 | * 4/1997 | Gloyd et al. ......................... 600/22 |
| 5,792,041 | * 8/1998 | Kobayashi et al. .................. 600/22 |
| 5,797,833 | * 8/1998 | Kobayashi et al. .................. 600/22 |
| 5,878,190 | 3/1999 | Gloyd et al. . |
| 5,897,485 | * 4/1999 | Koch ................................... 600/22 |
| 6,024,694 | * 2/2000 | Goldberg et al. .................... 600/22 |
| 6,090,036 | * 7/2000 | Kobayashi et al. .................. 600/22 |

* cited by examiner

Primary Examiner—Teresa Walberg
Assistant Examiner—Leonid Fastovsky
(74) Attorney, Agent, or Firm—Roger M. Rathbun

(57) ABSTRACT

A humidifier for use with an infant incubator is disclosed that has a housing and a reservoir. The reservoir is pivotally affixed to the housing so that it can be tilted from its upright position where it actively provides the heated water vapor to the incubator and a tilted position where water can be added to the reservoir. A heater extends into the reservoir to heat a localized volume of water. The reservoir is also removable from the housing but is constrained in its movement generally along the axis of the heater so as to prevent damage to the heater if the reservoir is immediately tilted during its removal or reinstallation.

21 Claims, 7 Drawing Sheets

HUMIDIFIER FOR INFANT WARMING APPARATUS

This application claims benefits 60/170,275 filed Dec. 11, 1999 which claims benefit of 60/182,135 filed Feb. 12, 2000.

BACKGROUND

The present invention relates to an infant warming apparatus and, more particularly, to a humidifier for adding moisture to the environment within the infant care apparatus.

There are, of course, many differing types of infant incubators currently available and most have some means of humidifying the air that is delivered to the infant compartment within the incubator. The infant compartment itself is a controlled environment within which the infant is positioned and where the environment is controlled to provide warmth and humidity to the infant for its wellbeing.

Typical of such humidifiers is the use of a reservoir that underlies the infant compartment and where the heated air to be delivered to that compartment passes over the water contained within the reservoir to increase the humidity, at a controlled rate, of the heated air that is then passed into the infant compartment. Thus, one of the common means of humidification for an infant incubator includes a means of causing the heated air to pass over a body of water, generally heated, where the warm air picks up water vapor and delivers the warm air laden with the water vapor to the infant compartment. One such humidification system is shown and described in U.S. Pat. No. 5,878,190 of Gloyd et al.

As a drawback of many present systems for humidification, the reservoirs are generally difficult to remove for cleaning and, additionally, some of the reservoirs normally slide horizontally from the humidifier in order to allow filling. The movement of the reservoir filed with water is somewhat difficult in the infant care environment and can cause the spilling of water. The water is also commonly spilled simply due to overfilling of the reservoir. The presence of spilled water is undesirable in that it can be a ground for contamination in the otherwise warm, damp surroundings.

SUMMARY OF THE INVENTION

Accordingly, the present invention relates to an infant incubator having a novel humidification system that injects the heated water vapor into the infant compartment of the incubator rather than pass the heated air over a body of water. In addition, the present invention includes a reservoir container that is affixed to the infant incubator in such a manner that it can be opened by simply tilting the reservoir with respect to the humidifier housing and the infant incubator and the filling can take place easily in the tilted position. Thus, when the reservoir is again returned to its upright condition, overfilling is avoided as the water level will be safely contained within the reservoir in its upright position.

Thus, when filled in its tilted position, the reservoir can be fully filled and yet the reservoir will not spill or be overfilled when the reservoir is returned to its upright operational position. The reservoir can be easily moved between its upright utile position and its tilted, filling position by the user.

Too, the water reservoir of the present invention is easily removable from the incubator by the user when it is desired to clean the reservoir. A heater extends downwardly into the reservoir to selectively heat a limited amount of water in the reservoir to provide rapid and controlled heating of the water and to inject the heated water vapor into the infant compartment. As a further feature, when the water reservoir is removed, its movement is controlled such that it is removable along a path that prevents the reservoir from breaking or bending the heater that extends downwardly into that reservoir.

In carrying out the present invention, there is a plastic reservoir container that is transparent to the extent that the level of water can be visually perceived from external of the reservoir and the incubator. In its upright position delivering heated water vapor to the incubator, the reservoir is normally locked in position by a forward, upward edge of the reservoir that is in abutment with a outward lip of the housing. That reservoir is affixed to the humidifier housing by means of a pair of resilient latches that are biased upwardly but can, by the user, be pushed downwardly to disengage the forward edge of the reservoir from the outward lip of the housing to free the reservoir from its position mounted to the housing of the humidifier. The reservoir is designed so as to allow the reservoir to be tilted outwardly a controlled or predetermined movement for filling the reservoir with water yet the reservoir is still securely retained to the housing of the humidifier. The tilting of the reservoir is also constrained to a predetermined angular movement and is held in the tilted position for adding water to the reservoir. In the preferred embodiment, the reservoir is held in the tilted position by means of an abrupt shoulder formed on the reservoir that also comes into engagement with the outward lip of the housing to enable the reservoir to be easily and safely tilted to the filling position.

The interaction of specially designed flanges on the reservoir and the housing of the humidifier also allows the resilient latch to be maneuvered and released to allow the reservoir to be completely removed from the humidifier housing for cleaning. As such, those interacting flanges require that the reservoir be removed by dropping it straight downwardly and not twisted in its removal process so as to prevent the breaking of the heater that depends downwardly into the reservoir from the humidifier housing to heat the water in a localized area.

These and other features and advantages of the present invention will become more readily apparent during the following detailed description taken in conjunction with the drawings herein.

DETAILED DESCRIPTION OF THE INVENTION

Figure 1:
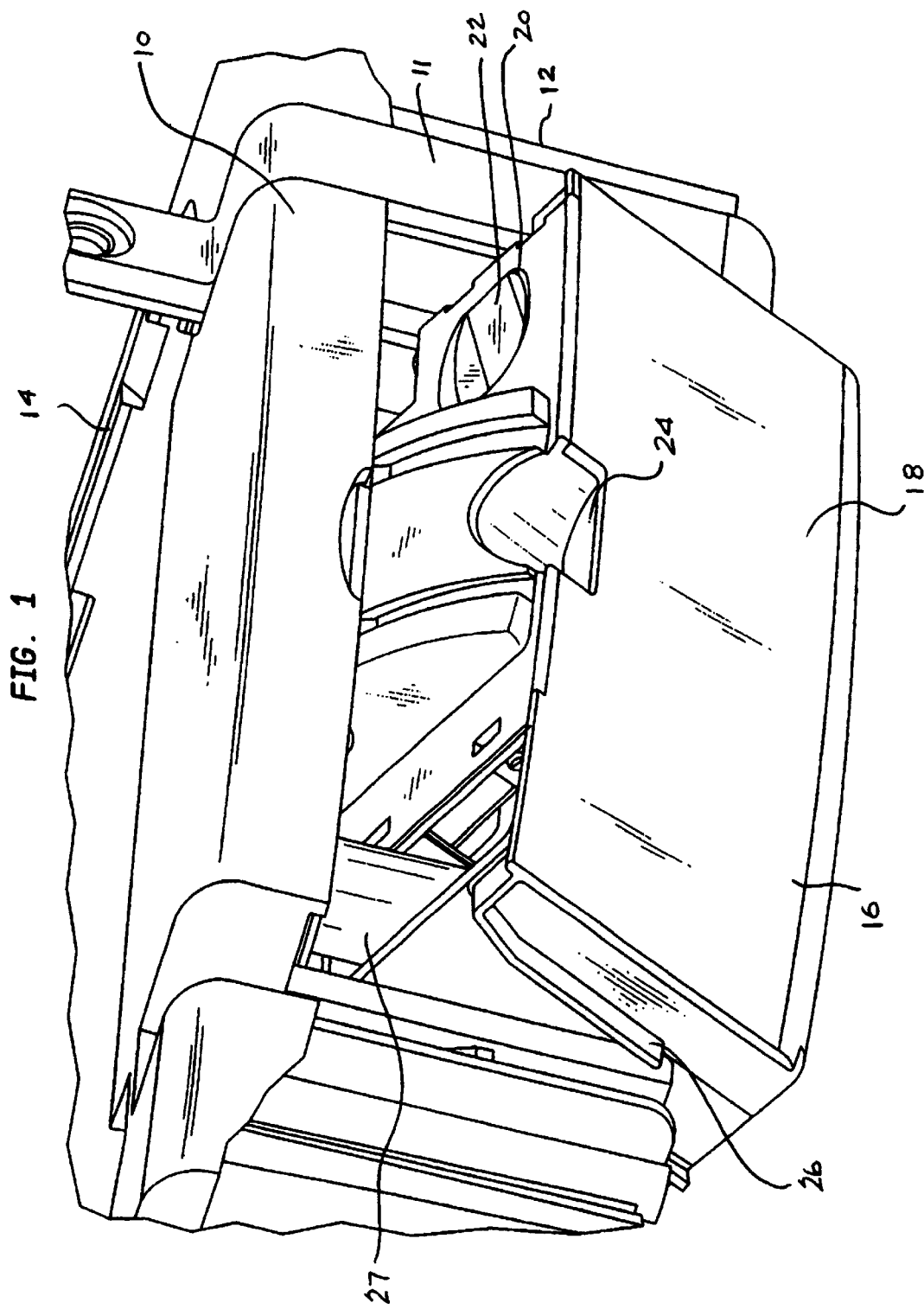
FIG. 1 is a perspective view of the humidifier of the present invention in its filling position.

Referring now to FIG. 1, there is shown a perspective view of the humidifier 10 constructed in accordance with the present invention and, as shown, comprises a housing 11 shown affixed to the chassis 12 of an incubator 14. As shown, the humidifier 10 includes a reservoir 16 that, as will be explained, is removable from the housing 11 of the incubator 14 for cleaning. Internal of the reservoir 16 is a volume to contain the water to be heated and vaporized and an external face 18 of the reservoir 16 is transparent so that the user can visually see and monitor the level of the water contained within the reservoir 16.

In the position as shown in FIG. 1, the reservoir 16 is in its filling position such that a filler opening 20 is available with a cover 22 that can be removed by the user to pour water into the reservoir 16 for filling the reservoir 16. As will be seen, the reservoir 16 can be moved to its filling position by the user easily and without removing the reservoir 16 from the housing 11 of the humidifier 10. An inset 24 is formed in the reservoir 16 to enable the user to fit a finger or thumb into the inset 24 to move the reservoir 16 to the filling position shown and will be later explained.

Also shown in FIG. 1 is a front flange 26 that extends outwardly from the side of the reservoir 16 and there is a similar flange on the opposite side of the reservoir 16 in the same configuration and position. As seen, the front flange 26 extends downwardly from the top of the reservoir 16 and generally extends inwardly as the front flange extends downwardly along the side of the reservoir 16. A heater 27 is also shown and which extends downwardly from the housing 11 of the reservoir 10 and heats the water in a confined area.

Figure 2:
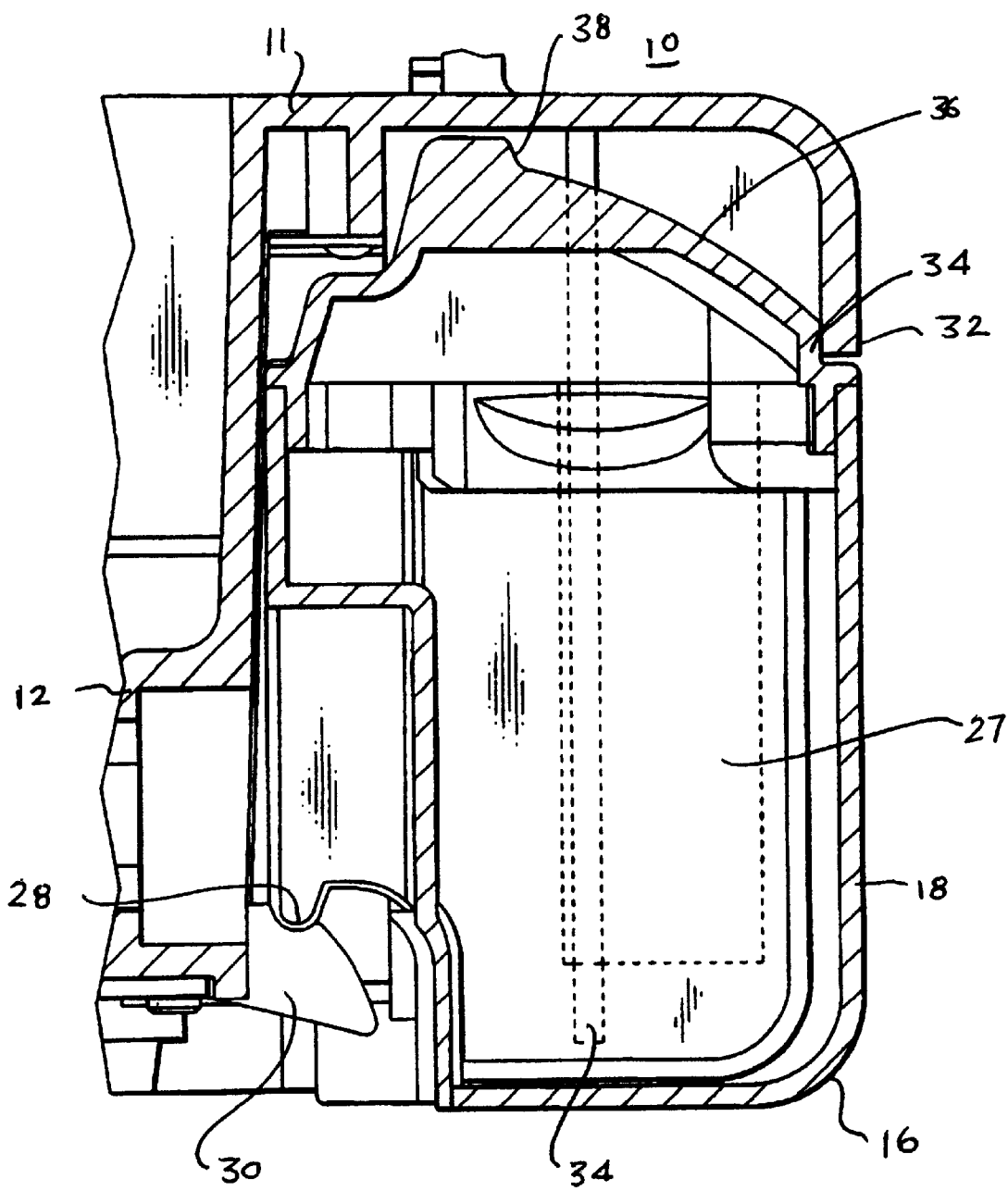
FIG. 2 is a side cross sectional view of the reservoir and in its upright, operative position providing humidification to the infant compartment.

Turning now to FIG. 2, there is shown a side cross sectional view of the reservoir 16 in its upright, operative position with respect to the housing 11 of the humidifier 10. As can be seen, the reservoir 16 has a downwardly extending rounded lower edge 28 that rests on and is supported by a resilient latch 30 that is affixed to the housing 11 of humidifier 10. The resilient latch 30 is spring loaded and thus is movable with respect to the housing 11 as will be explained. In the position shown in FIG. 2, the resilient latch 30 is in its upward position and is biased toward that position to hold the lower edge 28 of the reservoir 16 in upright, operative position of FIG. 2. The housing 11 also includes a front downwardly curled lip 32 that also serves to hold the reservoir 16 in the upright, operative position by providing a support for the upper front edge 34 of the reservoir 16.

Accordingly, as shown, the use of the resilient latch 30 and the confining of the upper front edge 34 by the lip 32 retains the reservoir 16 in the upright, operative position as shown in FIG. 2.

Figure 3:
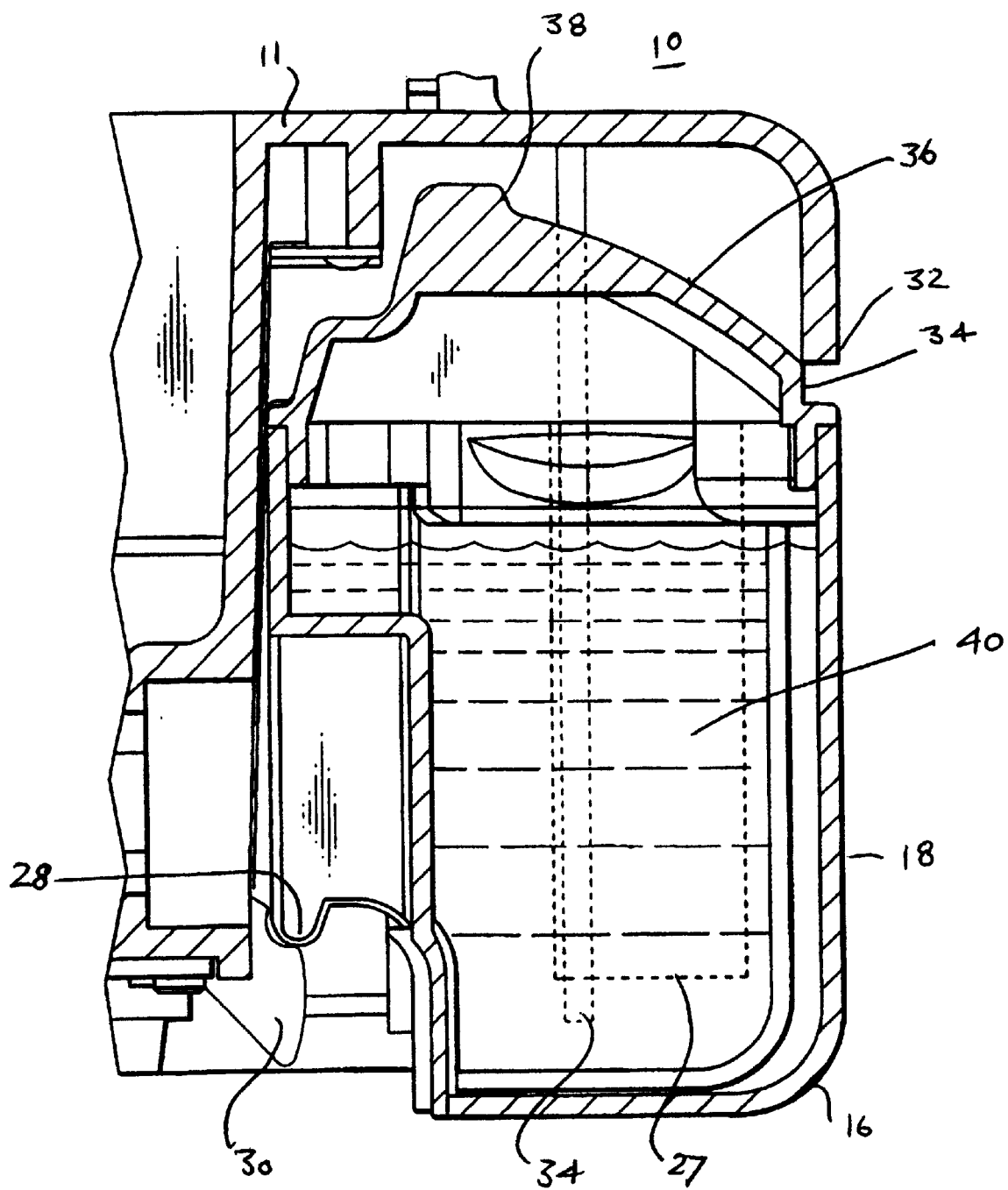
FIG. 3 is side cross sectional view of the humidifier of the present invention partially removed from its upright, operative position.

Turning now to FIG. 3, there is shown a cross sectional view of the reservoir 16 of the present invention that has been moved downwardly against the bias of the resilient latch 30. In this Fig., therefore, the user has manipulated the reservoir 16 by pushing downwardly on the inset 24 (FIG. 1) to lower the reservoir 16 such that the upper front edge 34 is no longer contained by the lip 32. At this position, the reservoir 16 is free to tilt outwardly a controlled angular amount and the tipping action is stabilized by the lip 32 riding along the curved surface 36. The curved surface end in its upward direction with a abrupt shoulder 38. As can also be seen in the Figure, the level of water 40 is shown and will be later discussed.

Figure 4:
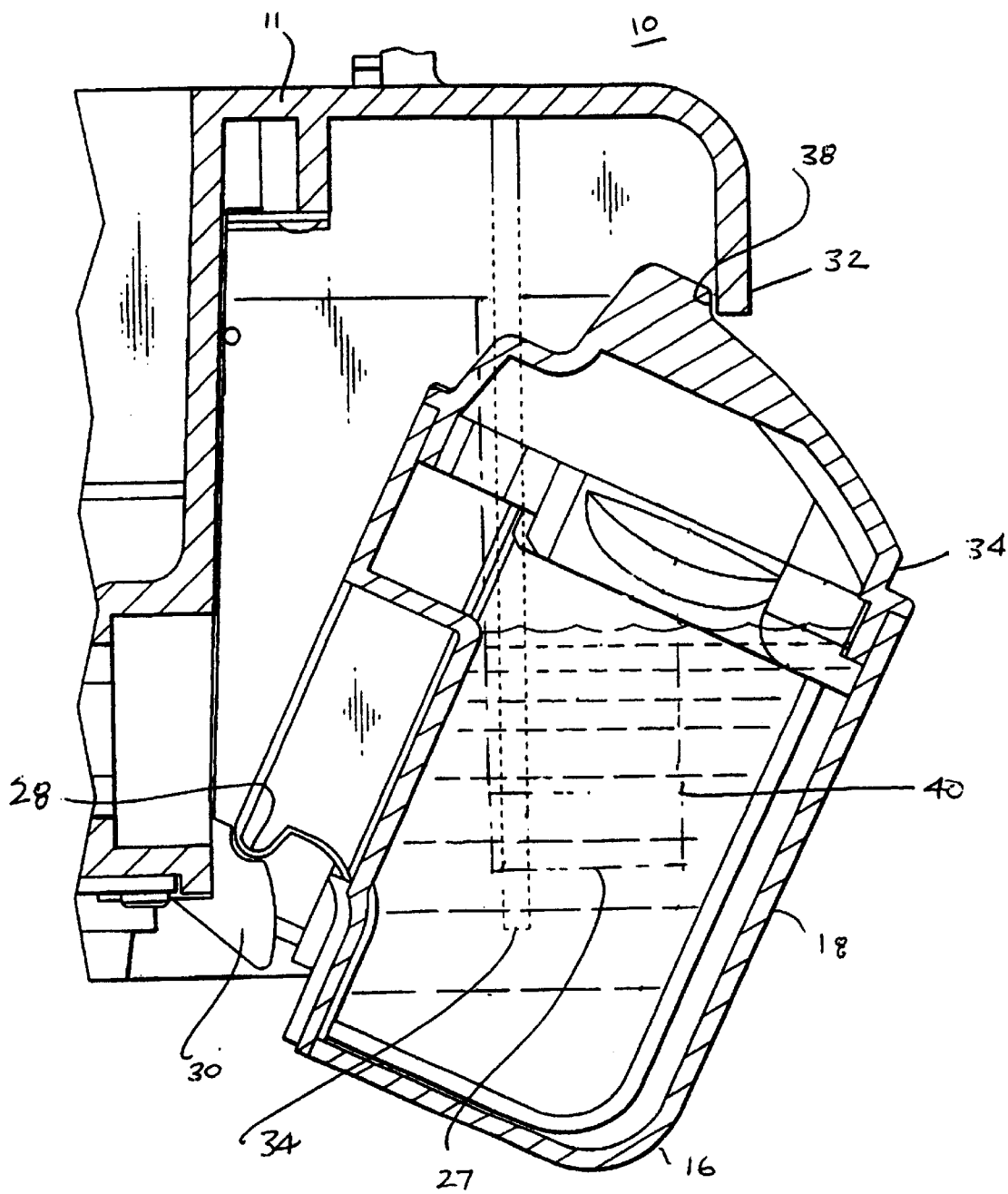
FIG. 4 is a side cross sectional view of the humidifier with its reservoir in its filling position.

Turning next to FIG. 4, there is shown a further cross sectional view of the reservoir 16 but in the tipped or filling position. Thus, in the position shown, the reservoir 16 filler opening (FIG. 1) is available to the user and water can be poured into the reservoir 16. Also, in the tilted position of FIG. 4, the reservoir is still held in its position affixed to the housing 11 by means of the resilient latch 30 in contact with the lower edge 28 of the reservoir and further held in the tilted or filing position by the abrupt shoulder 38 abutting against the lip 32, thereby holding the reservoir 16 firmly in position to the housing 11 to allow the reservoir 16 to be filled with water by the user.

It should be noted that the level of the water 40 as shown in FIG. 4 is such that the user can fill the water to its uppermost level, since it is in a tilted position, and when the reservoir 16 is returned to its upright, operative position of FIG. 3, the water level will effectively become lowered in the reservoir 16 as the reservoir becomes upright, thus the user cannot over fill the reservoir 16 due to the use of a tilting mechanism as opposed to a sliding movement or other means to make the filler of the reservoir available to the user for filling.

Figure 5:
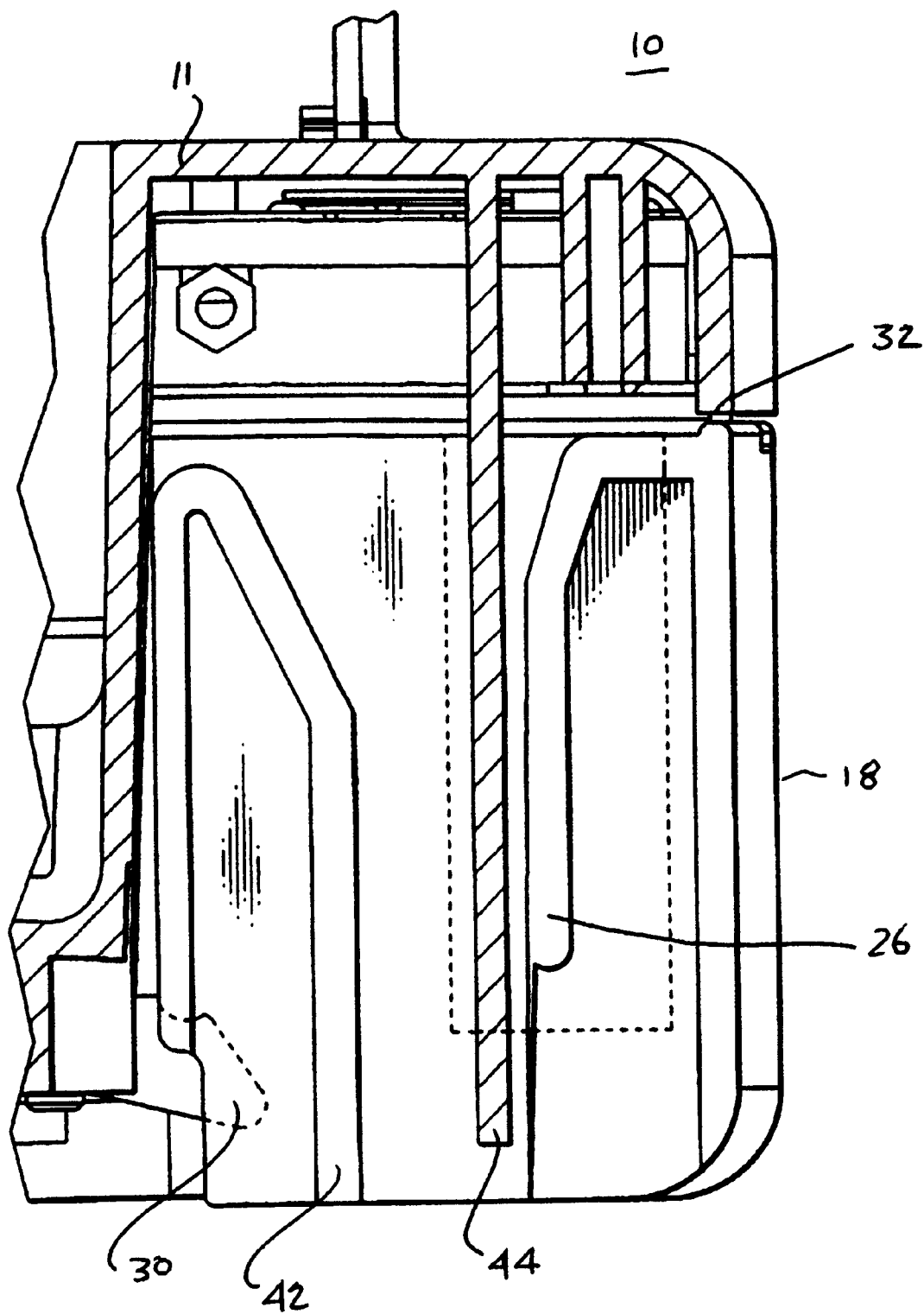
FIG. 5 is a side cross sectional view of the present showing the flanges of the reservoir and the chassis of the reservoir.

Turning now to FIG. 5, there is shown a cross section showing the sides of the reservoir 16 and the inner surfaces of the housing 11 into which the reservoir 16 is interfitted. As shown, there are front flanges 26 (also shown in FIG. 1) and rear flanges 42, both formed at both sides of the reservoir 16 that extend outwardly from the sides of the reservoir 16. Similarly, there are generally vertical housing flanges 44, formed in the surfaces of the housing 11 and extending outwardly therefrom. As shown in FIG. 5, the vertical housing flange 44 is positioned intermediate the front flange 26 and rear flange 42 such that vertical housing flange 44 interferes with the front and rear flanges 26, 42 of the reservoir 16. As such, the vertical housing flange 44 serves as a guide in the removal of the reservoir 16 from the housing 11.

Figure 6:
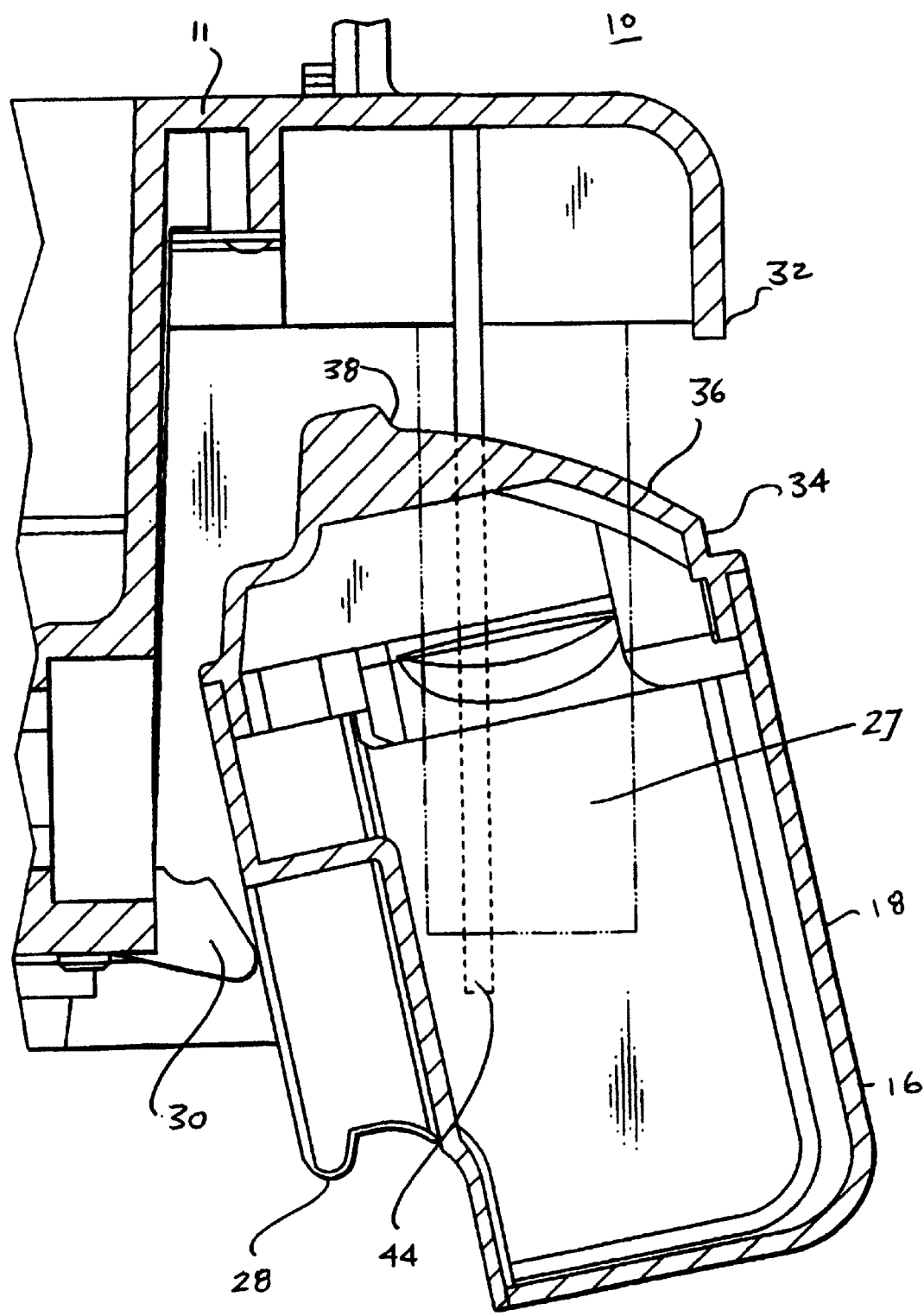
FIG. 6 is a side cross sectional view of the reservoir of the present invention as it is being removed from the humidifier.

Thus, in removing the reservoir for cleaning and the like, the resilient latch 30 is released from its contact with the lower edge 28 of the reservoir 16 and the reservoir can be moved vertically downwardly as shown in FIG. 6 and cannot be angled outwardly until the heater 27 has been cleared. That vertical restraint is caused by the vertical housing flange 44 that interferes with both the front and rear flanges 26, 44 of the reservoir 16 so that the reservoir 16 cannot be immediately pulled or angled outwardly but must be lowered generally vertically. Thus the use of the vertical housing flange 44 protects the heater 27 that depends downwardly into the reservoir 16 from the housing 11 and the heater 27 cannot be broken off by a user immediately pulling the reservoir 16 outwardly to remove the reservoir 16. Instead, by the interaction of the flanges, the reservoir 16 must be lowered vertically downwardly until the front and rear flanges 26, 44 clear the lower end of the vertical housing flange 44 and, only at that point, can the reservoir 16 be angled outwardly away from the generally vertical direction. At that point, the heater 27 has been sufficiently uncovered so as to protect it from damage.

Figure 7:
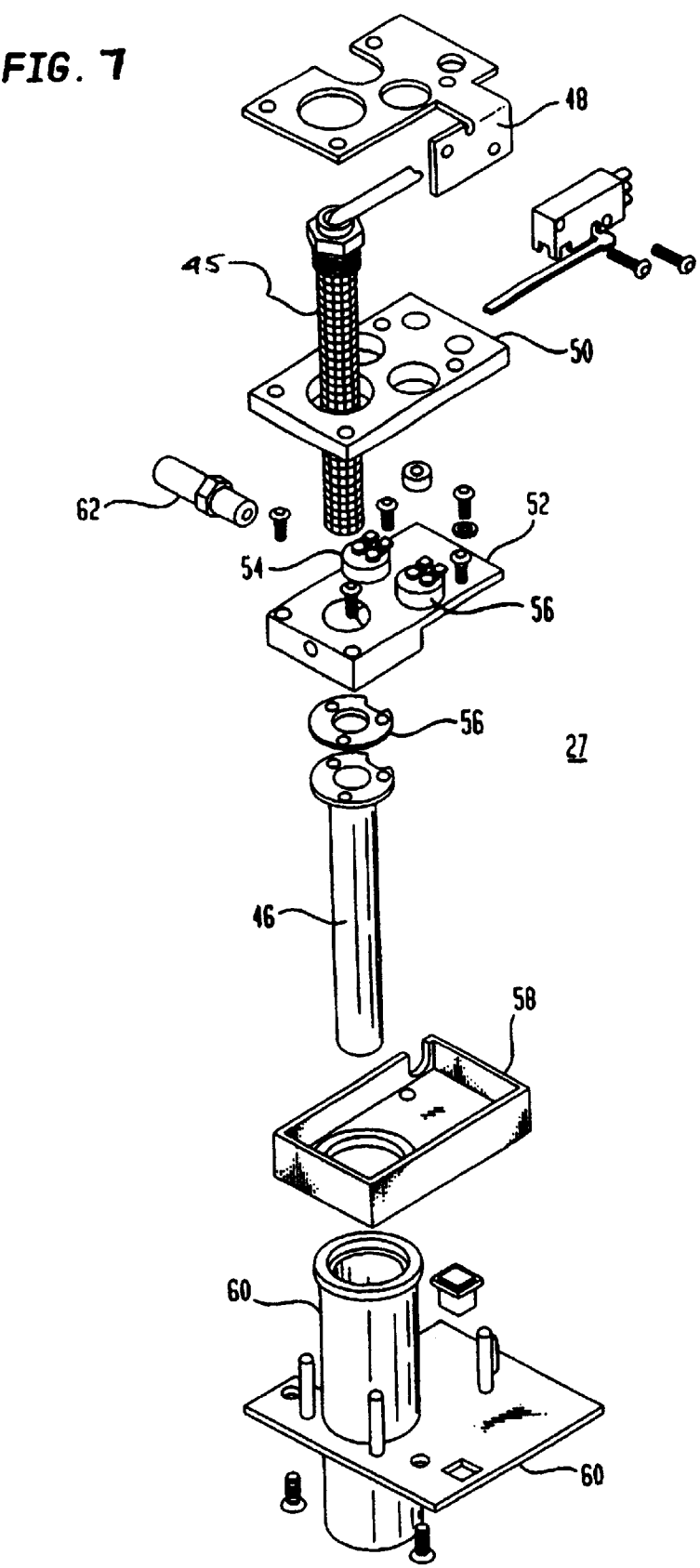
FIG. 7 is an exploded view of the heater used in the humidifier of the present invention.

Finally, in FIG. 7 there is an exploded view of the heater 27 and which includes a cartridge heater element 45 and is inserted into an aluminum sheath 46. A top bracket 48 affixes the heater 27 to the housing 11 of the humidifier and includes a rubber insulator 50 for insulation and a middle bracket 52 having heat sensors 54 and 56, one of which senses low water and the other is a safety sensor in series with the heater element 44. A further flexible washer 56 seals the aluminum sheath 46 to prevent water from contacting the heater element 44. Further, there is a rubber insulator 58 and a bottom bracket 60 the hold a plastic container 60 that depends downwardly into the water within the reservoir.

Thus, as the plastic container 60 is immersed in the water within the reservoir 16, the plastic container 60 becomes filled with water and the heater element 44 can heat only a localized quantity of water contained in the plastic container 60 and not the entire reservoir filled with water. Thus, with the reservoir filled, there is sufficient quantity of water to provide humidification for a long period of time without refilling, however, at the same time, the heater does not have to heat the entire quantity of water but only the small localized quantity of water that is within the plastic container 60.

Accordingly, the heated water vapor is collected in the plastic container 60 and rises to exit from the plastic container 60 out of the outlet 62 to be directly introduced into the infant compartment of an incubator.

Those skilled in the art will readily recognize numerous adaptations and modifications which can be made to the humidifier of the present invention which will result in an improved apparatus, yet all of which will fall within the scope and spirit of the present invention as defined in the following claims. Accordingly, the invention is to be limited only by the following claims and their equivalents.

I claim:

1. A humidifier for an infant incubator, said humidifier comprising a housing and a reservoir pivotally affixed to said housing, a heater extending from said housing into said reservoir to heat water contained within said reservoir to create water vapor, said reservoir being movable between an upright position where the humidifier is operational to provide water vapor to the infant incubator and a tilted position where said reservoir is tilted from said upright position to allow the adding of water to said reservoir.

2. A humidifier for an infant incubator as defined in claim 1 wherein said housing includes a spring biased latch and said reservoir is held in said upright position by said spring biased latch.

3. A humidifier for an infant incubator as defined in claim 2 wherein said reservoir is locked in said upright position and said reservoir is movable from said upright position to said tilted position by moving said reservoir against said spring biased latch to release said reservoir to unlock said reservoir to allow said reservoir to be moved from said upright position to said tilted position.

4. A humidifier for an infant incubator as defined in claim 3 wherein said housing includes an outward lip and said reservoir includes an upper front edge that abuts against said outward lip of said housing to maintain said reservoir in said upright position.

5. A humidifier for an infant incubator as defined in claim 4 wherein said reservoir is movable downwardly against said spring biased latch to release said upper front edge of said reservoir from said outward lip of said housing.

6. A humidifier for an infant incubator as defined in claim 5 wherein said reservoir has an abrupt shoulder adapted to abut against and be retained by said outward lip of said housing when said reservoir is in said tilted position.

7. A humidifier for an infant incubator as defined in claim 6 wherein said reservoir has a curved outer surface intermediate said upper front edge and said abrupt shoulder adapted to substantially continually contact said outward lip as said reservoir is moved between said upright and said tilted positions.

8. A humidifier for an infant incubator, said humidifier comprising a housing and a reservoir removably affixed to said housing, a heater extending from said housing downwardly into said reservoir to heat water contained within said reservoir to create water vapor to introduce water vapor into said incubator, said heater having a main longitudinal axis, means to constrain said reservoir to movement generally parallel to said main longitudinal axis of said heater to remove said reservoir from said housing and to replace said reservoir to said housing.

9. A humidifier for an infant incubator as defined in claim 8 wherein said means to constrain said movement of said reservoir comprises a first elongated flange extending outwardly from said housing and generally parallel to said axis of said heater and a second elongated flange extending outwardly from said reservoir and generally parallel to said axis of said heater, said first and second flanges adapted to interfere with each other to constrain the movement of said reservoir generally parallel to said main longitudinal axis of said heater.

10. An incubator for containing an infant, said incubator having an infant compartment and a humidifier adapted to generate heated water vapor for injecting the heated water vapor into said infant compartment, said humidifier further comprising a housing and a reservoir pivotally affixed to said housing, a heater extending from said housing into said reservoir to heat water contained within said reservoir, means to inject the water vapor from said reservoir into said infant compartment, said reservoir being movable between an upright position where the humidifier is operational to provide water vapor to the infant incubator and a tilted position where said reservoir is tilted from said upright position to allow the adding of water to said reservoir.

11. An incubator for containing an infant as defined in claim 10 wherein said heater comprises a cylindrical container extending into said reservoir to be submerged in water contained within said reservoir to allow water to enter said cylindrical container, and an electric heater within said cylinder container, said electric heater adapted to heat the water confined within said cylindrical container.

12. An incubator for containing and infant as defined in claim 11 wherein said cylindrical container extends vertically downwardly into said reservoir.

13. An incubator for containing an infant as defined in claim 10 wherein said cylindrical container is comprised of a plastic material.

14. An incubator for containing an infant, said incubator having an infant compartment and a humidifier adapted to generate heated water vapor for injecting the heated water vapor into said infant compartment, said humidifier further comprising a housing and a reservoir containing water affixed to said housing, a heater extending from said housing into said reservoir to heat water contained within said reservoir, said heater comprising a container extending into said reservoir to be submerged in the water contained within said reservoir to allow water to enter said container, and a electric heater within said container, said electric heater adapted to heat the water confined within said container to form water vapor and means to inject the water vapor from said container into said infant compartment.

15. An incubator for containing an infant as defined in claim 14 wherein said reservoir is removably affixed to said housing.

16. An incubator for containing an infant as defined in claim 14 wherein said reservoir is pivotally affixed to said reservoir.

17. An incubator for containing an infant as defined in claim 16 wherein said reservoir is pivotal between an upright position where said water vapor is generated and a tilted position angularly displaced from said upright position wherein said reservoir can be filled with water.

18. An incubator for containing an infant as defined in claim 17 wherein said container is a cylindrical container.

19. An incubator for containing an infant as defined in claim 14 wherein said electric heater is a cartridge heater extending downwardly within said container.

20. An incubator for containing an infant as defined in claim 19 wherein said cartridge heater is contained within a sheath to prevent water from contacting said cartridge heater.

21. An incubator for containing an infant as defined in claim 20 wherein said sheath is a metallic sheath.

* * * * *